(12) United States Patent
Foos et al.

(10) Patent No.: US 8,718,348 B2
(45) Date of Patent: May 6, 2014

(54) GRID SUPPRESSION IN IMAGING

(75) Inventors: David H. Foos, Webster, NY (US); John Yorkston, Penfield, NY (US); Xiaohuo Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 638 days.

(21) Appl. No.: 12/840,351

(22) Filed: Jul. 21, 2010

(65) Prior Publication Data

US 2011/0033101 A1 Feb. 10, 2011

Related U.S. Application Data

(60) Provisional application No. 61/232,015, filed on Aug. 7, 2009.

(51) Int. Cl.
*G06K 9/00* (2006.01)
*G06T 7/00* (2006.01)

(52) U.S. Cl.
CPC .................................. *G06T 7/0012* (2013.01)

USPC .......................................... 382/132; 382/128

(58) Field of Classification Search
USPC ........................... 382/132, 128; 378/62, 98.9
See application file for complete search history.

(56) References Cited

U.S. PATENT DOCUMENTS

| | | | |
|---|---|---|---|
| 5,661,818 A | 8/1997 | Gaborski et al. | |
| 6,269,176 B1 * | 7/2001 | Barski et al. | 382/128 |
| 6,816,572 B2 | 11/2004 | Jabri et al. | |
| 7,627,084 B2 * | 12/2009 | Jabri et al. | 378/62 |

* cited by examiner

*Primary Examiner* — Michelle L Le

(57) ABSTRACT

A method for providing a diagnostic image as a combination of two or more images executed, at least in part, on a control logic processor. The method includes obtaining at least first and second image data of a subject and analyzing both the first and second image data to identify at least grid orientation and spacing. Grid suppression is applied to the first and second image data and the grid suppressed first and second image data is pre-processed. The method then combines the grid suppressed first and second image data and decomposes the combined data to obtain one or more diagnostic images for display. The one or more diagnostic images are displayed on a display that is associated with the control logic processor.

15 Claims, 7 Drawing Sheets

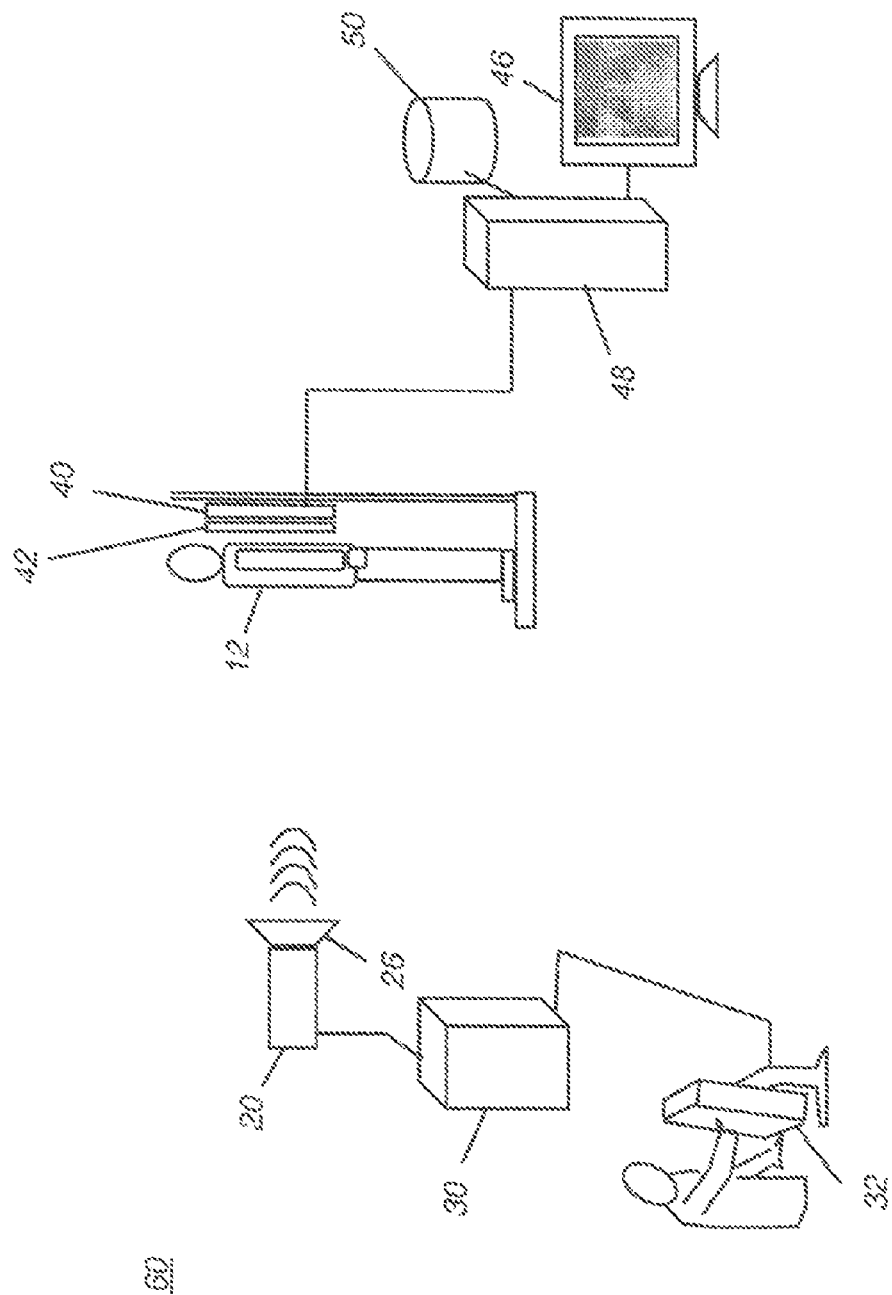

GRID SUPPRESSION IN IMAGING

CROSS REFERENCE TO RELATED APPLICATIONS

Priority is claimed from U.S. Ser. No. 61/232,015, provisionally filed on Aug. 7, 2009, entitled "GRID SUPPRESSION FOR DUAL ENERGY AND COMPOSITE IMAGING", in the names of Foos et al., commonly assigned and incorporated herein by reference.

FIELD OF THE INVENTION

The invention relates generally to the field of diagnostic imaging and more particularly to methods for grid detection and suppression in imaging modalities that combine two or more images of the same patient to obtain a diagnostic image.

BACKGROUND OF THE INVENTION

Linear grids are anti-scatter devices that are used to improve contrast and the signal to noise ratio in radiographic images. A grid typically consists of a series of lead foil strips separated by spacers that are transmissive to x-rays. The spacing of the strips determines the grid frequency, and the height-to-distance between lead strips determines the grid ratio. Grids can be oriented horizontally or vertically relative to the imaging medium.

There are two general methods of use for grids: moving (Bucky-Potter configuration) and stationary. For moving type grids, the shadows of the lead strips are blurred out by motion, which can be either reciprocating or unidirectional (single stroke). For stationary grids, the shadows of the lead strips are imposed onto the radiographic image. In cases where a moving grid does not reciprocate properly or the time of exposure is faster than the time it takes for the grid to move, the resulting image can also exhibit unwanted lead strip shadows.

The pattern formed by the grids can cause image artifacts that resemble moire patterns and can hinder diagnostic interpretation of the x-ray image. One undesirable affect of grid patterns is aliasing, introduced in discrete sampling of the image by the scanning system. Factors that contribute to the aliasing are the grid resolution (grid line frequency), the sampling frequency, and the modulation transfer function (MTF) of the image acquisition device. The most typical manifestation of the problem occurs when an image is reduced in size for the purpose of soft copy presentation on a display monitor, such as on a liquid-crystal display or a cathode-ray tube (CRT), for example.

Grid use in x-ray imaging is optional and different radiology departments may have different practices related to grid use. Thus, a first step in grid artifact correction is detection of grid effects in the image content, due either to the use of a stationary grid or to malfunction of a moving Bucky-Potter grid device. One technique for grid detection is described in U.S. Pat. No. 5,661,818, issued Aug. 26, 1997, to Gaborski et. al., who describe a grid detection method that bases its detection decision on a double auto-correlation calculation. Variances are measured independently, both horizontally and vertically, and a statistical F test is performed to determine if the variances are the same over a randomly chosen sampling of locations within the image. Votes are then tallied and if a majority indicates that the variances are different, a decision is made in favor of a grid being present. This method is useful for grid detection; however, it does not provide any characteristic information about the nature of the grid that has been detected, nor does it provide information on variables such as the grid line frequency(s), the noise power of the grid, or other parameters. This type of information is important for an automated solution that compensates for grid aliasing and suppressing the grid lines.

Once a grid is detected, the grid shadows are preferably either removed or suppressed. These shadows can be considered a form of correlated noise in the image. Well known methods exist to characterize and eliminate correlated noise. However, it can be difficult to apply correction, since the frequency of grid lines within a given device can be quite variable due, in part, to the manual nature of the manufacturing process. Because of this, 2-D Fourier filtering methods and other methods that use bandstop filters can be less straightforward and prone to the introduction of artifacts if the filter is incorrectly designed. Also, in order to meet near real-time speed requirements, the commercial viability of such methods generally requires special-purpose, dedicated processing hardware due to the relatively large format of the image (2K×2K up to 4K×4K, at 12 bits/pixel). Spatial filtering is the next best choice, such as convolution with a blurring filter. But such a solution, if applied indiscriminately, often results in a global reduction of image detail. Adaptive filtering methods have been found to be appropriate for grid detection and suppression.

The problem of grid detection and suppression is further complicated where Dual-Energy (DE) imaging is used. In Dual-Energy (DE) radiography, two x-ray images of a subject are acquired by a Digital Radiography (DR) system at different energy levels, wherein the images are obtained either at the same time (using two different sets of imaging pixel sensors with one or more suitable filters on the detector) or successively, within a short time interval. The low-energy image is generally acquired first, with an exposure interval typically in the 100-300 msec range. The high-energy image is then acquired, typically within 1 second of the low-energy image, with an exposure interval in the 10-30 msec range. The two images are registered to each other, then used to decompose the imaged anatomy into separate soft-tissue and bone images. DE imaging and image processing for DE images is described, for example, in U.S. Pat. No. 6,816,572 entitled "Method, System and Computer Product for Processing Dual-Energy Images" to Jabri et al. In general, a grid is needed for DE imaging in order to reduce scatter, particularly for the low-energy image.

U.S. Pat. No. 7,627,084 entitled "Image Acquisition and Processing Chain for Dual-Energy Radiography Using a Portable Flat Panel Detector" to Jabri et al., addresses issues related to image processing and noise correction for DE imaging, including grid artifact elimination. In the sequence described by Jabri et al., various pre-processing and post-processing techniques are used for both the high-energy and low-energy images. Grid artifact elimination is applied separately to each soft tissue and bone image in a post-processing sequence that follows image decomposition.

It has been noted, however, that a number of problems result when applying grid suppression to the decomposed soft tissue and bone images. For example, aliasing can cause problems with identifying the appropriate frequency and spatial locations from which to remove the offending grid line artifacts. A further complicating factor relates to the relative contrast of the grid lines in each of the high and low energy images. Because these contrast values can be different and can have a different impact on processing each image type, the results of grid suppression can be disappointing when used in image post-processing.

Dual energy imaging is one type of imaging technique in a larger class of imaging methods that generate composite images, that is, images that are obtained by combining two or more images taken at different energy levels, at different angles, or with a change to some other variable between images.

Another imaging modality in this class that uses combined image data is limited-angle digital tomosynthesis (DTS). In tomosynthesis, the relative positions of the x-ray source and detector are changed between each of two or more images, and the images are then combined to produce 3-D views of a subject. DTS is used, for example, in angiography, chest imaging, mammography, dental imaging, and orthopaedic imaging.

Yet another type of imaging modality that uses combined image data from multiple views is cone beam computerized tomography (CBCT).

With both DTS and CBCT methods, some form of grid detection and suppression may be needed, as is needed with DE imaging.

Thus, there is a need for an image processing method that provides anti-scatter grid suppression for dual energy, digital tomosynthesis, computerized tomography, and for other types of composite imaging.

SUMMARY OF THE INVENTION

An object of the present invention is to address the need for grid suppression in images obtained using dual energy imaging techniques. With this object in mind, the present invention provides a method for providing a diagnostic image as a combination of two or more images, the method comprising: obtaining at least first and second image data of a subject from an image detector and storing this image data in an electronic memory; analyzing at least one of the first and second image data to identify at least grid orientation and spacing; applying grid suppression to the first and second image data according to the identified grid orientation and spacing; preprocessing the grid-suppressed first and second image data; and combining the preprocessed first and second image data and decomposing the combined data to obtain one or more diagnostic images for display.

In some embodiments of the present invention, obtaining the at least first and second image data comprises obtaining the first image data at a first exposure and obtaining the second image data at a second exposure, different from the first exposure.

In some embodiments of the present invention, obtaining the at least first and second image data comprises obtaining the first image data at a first angle between a detector and a radiation source and obtaining the second image data at a second angle, different from the first angle.

In some embodiments of the present invention, decomposing the combined image data provides soft tissue and bone images.

In some embodiments of the present invention, applying grid suppression further comprises obtaining stored grid attribute data.

In some embodiments of the present invention, the image detector is a digital radiography detector.

From another aspect, the present invention provides a method for providing a diagnostic image as a combination of two or more images, the method comprising: obtaining at least first and second image data of a subject from an image detector and storing this image data in an electronic memory; analyzing at least one of the stored first and second image data to identify at least a grid orientation and a grid spacing; preprocessing the first and second image data; and combining the preprocessed first and second image data, applying grid suppression according to the identified grid orientation and spacing and decomposing the combined data to obtain one or more diagnostic images for display.

A feature of the present invention is its use of grid detection and suppression routines as part of image pre-processing for DE images.

An advantage of the present invention is that it uses information obtained from both low- and high-energy images in order to detect and suppress grid artifacts.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 7 is a schematic diagram of an imaging apparatus for providing dual energy (DE) imaging of a patient or other subject according to an embodiment of the present invention.

DETAILED DESCRIPTION OF THE INVENTION

Figure 1:
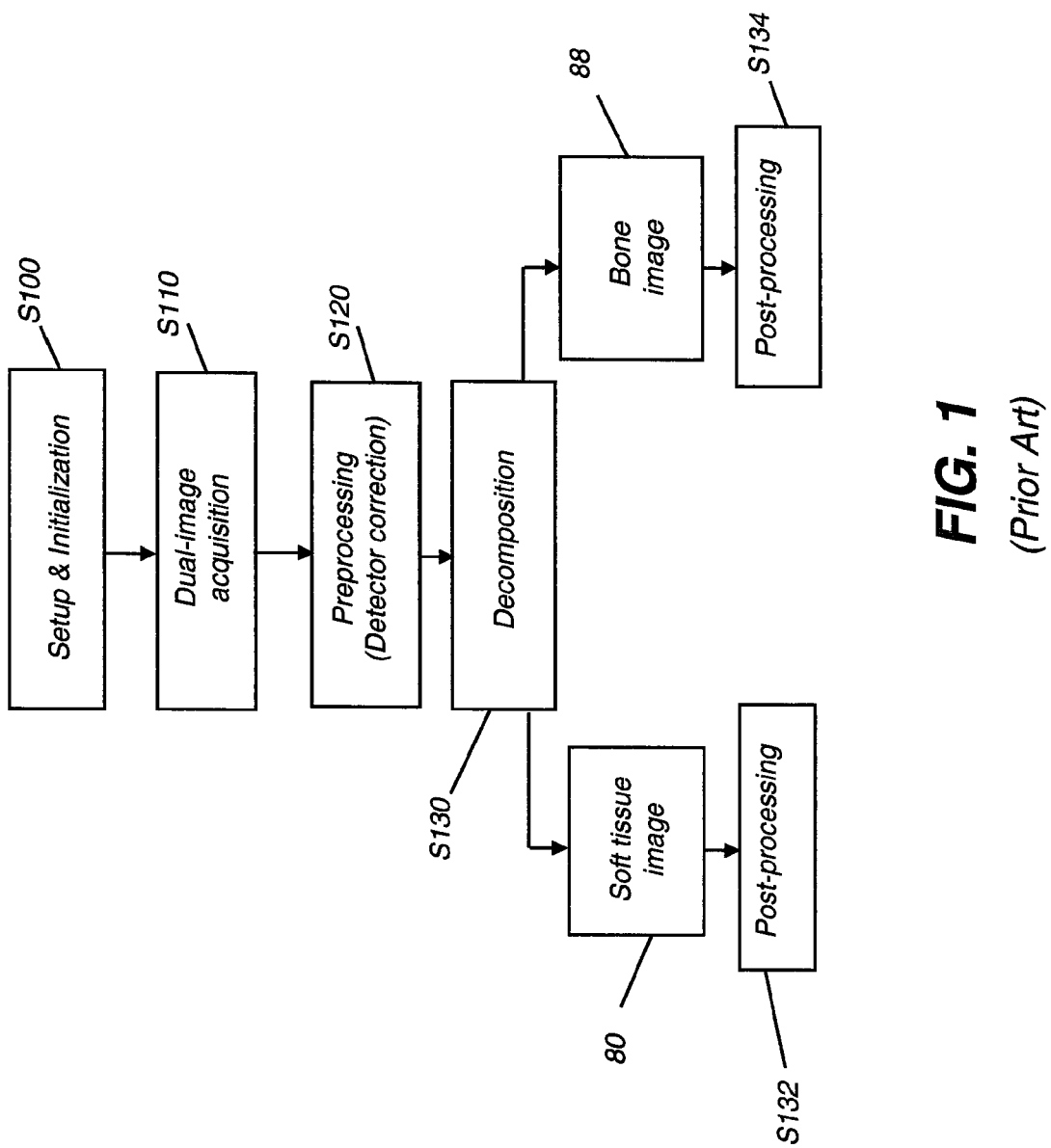
FIG. 1 shows conventional processing for dual energy imaging.

The following is a detailed description of the preferred embodiments of the invention, reference being made to the drawings in which the same reference numerals identify the same elements of structure in each of the several figures.

The method of the present invention executes on a computer or other type of control logic processor, which may include a dedicated microprocessor or similar device. A computer program product used in an embodiment of the present invention may include one or more storage media, for example; magnetic storage media such as magnetic disk or magnetic tape; optical storage media such as optical disk, optical tape, or machine readable bar code; solid-state electronic storage devices such as random access memory (RAM), or read-only memory (ROM); or any other physical device or media employed to store a computer program having instructions for configuring and controlling one or more computers to practice the method according to the present invention.

Embodiments of the present invention use image data taken at a digital detector, such as a Digital Radiography (DR) detector or a Computed Radiography (CR) detector. With the DR detector, the separate images can be obtained successively, using the same image pixel elements. Alternately, a DR detector having separate sets of pixel elements, with appropriate filters, can be envisioned. With a DR detector, a filter element is used in conjunction with the detector for at least one of the images.

Embodiments of the present invention address the problem of grid detection and suppression for dual energy (DE) images by analyzing and processing the raw image data obtained for both the low-energy (LE) image and the high-energy (HE) image that are obtained for dual energy (DE) imaging and suppressing grid artifacts early in the image processing sequence. This is in contrast to existing methods, as noted earlier in the background section, that attempt to eliminate grid artifacts in the soft tissue and bone images that are generated later in the sequence by the image decomposition process.

To better appreciate how the method of the present invention differs from and improves upon existing grid suppression processing for DE systems, it is first helpful to consider how these existing processes execute. Referring to FIG. 1, there is shown a logic flow sequence for conventional image processing with DE systems. A setup and initialization step S100 sets up the imaging technique and other parameters specific to DE imaging. This can include setting the kVp and mAs values, exposure times, and other technique-related variables. It also includes the necessary refresh and reset cycling of the DR detector prior to obtaining the low- and high-energy images in rapid succession. An image acquisition step S110 follows, in which the low-energy LE and high-energy HE images are successively or simultaneously taken and the results stored in an electronic memory for further processing. A preprocessing step S120 then follows, in which various detector correction algorithms are applied to the acquired data. This can include temperature-related correction, motion correction, and alignment processing, for example.

Following preprocessing step S120 in FIG. 1, a decomposition step S130 is then executed. Decomposition forms a soft tissue image 80 and a bone tissue image 88 by combining the registered LE and HE image data. Various mathematical methods, well known in the imaging arts, are used within decomposition step S130 for extracting the respective soft-tissue and bone image content from the LE and HE image data. A post-processing step S132 is then applied to soft-tissue image 80. Similarly, a post-processing step S134 is also applied to bone image 88. Conventional post-processing steps S132 and S134 can include grid correction, contrast matching, noise reduction, and processing for display rendering.

Figure 2:
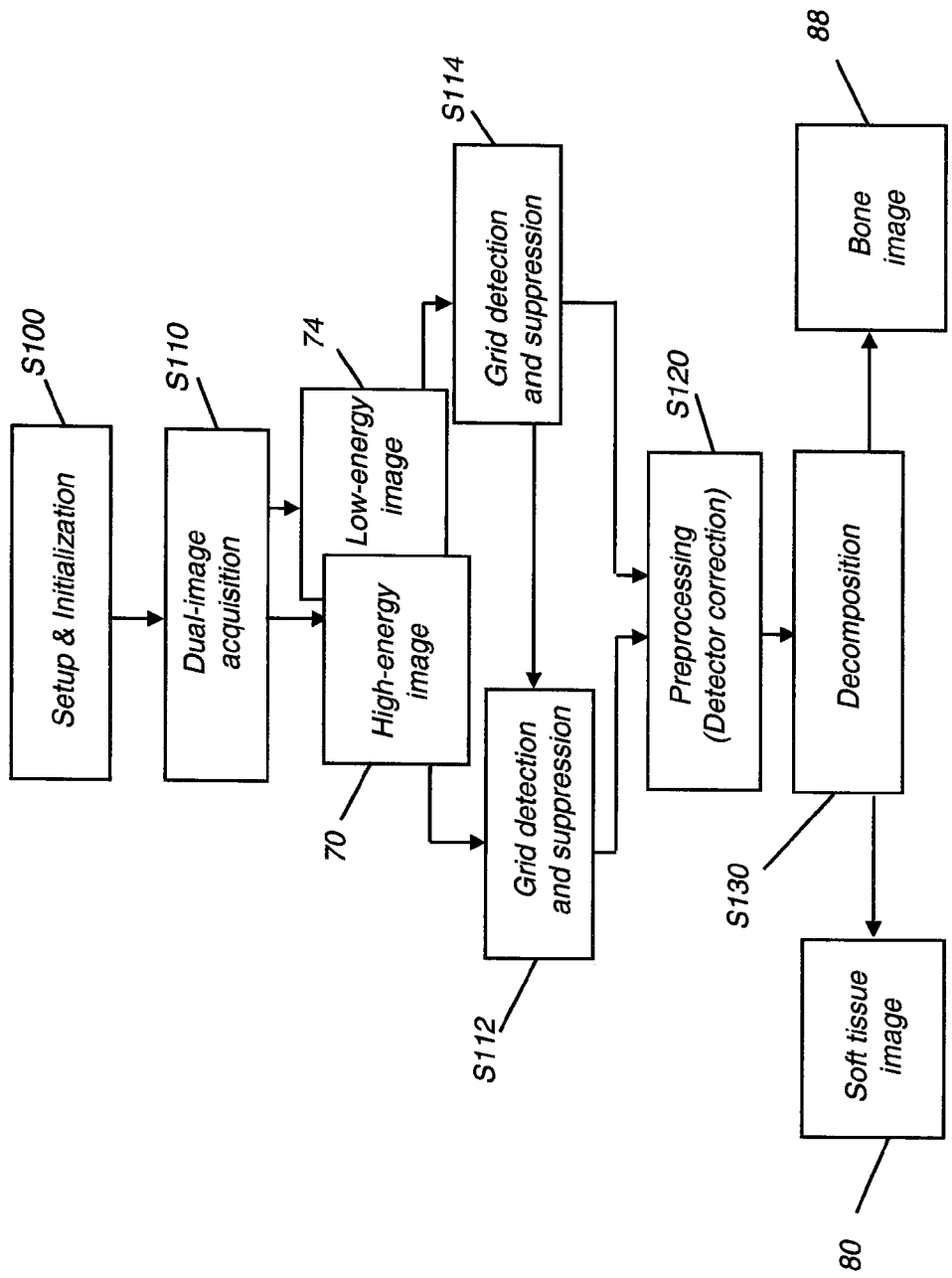
FIG. 2 shows processing for dual energy imaging according to one embodiment of the present invention.

The logic flow diagram of FIG. 2 shows how the method of the present invention changes conventional processing for DE imaging in one embodiment. Comparing this sequence to the basic sequence of FIG. 1, it can be seen that additional grid detection and suppression steps S112 and S114 are carried out on an obtained high-energy image 70 and an obtained low-energy image 74 in the sequence of FIG. 2. In particular, grid suppression is performed prior to preprocessing step S120 and before the image decomposition in step S130 that provides soft-tissue and bone images 80 and 88. Image decomposition thus uses the grid-suppressed low- and high-energy data.

Using the processing method shown in FIG. 2 offers adaptive grid suppression with a number of advantages over earlier, conventional methods for grid detection and suppression. One advantage relates to contrast of the grid lines. Conventional grid suppression operates on the combined data that has already been decomposed from low- and high-energy image data. However, the inventors have observed that the contrast of the grid lines in the low-energy image is generally higher than the contrast for the high-energy image. Grid effects can be more difficult to discern in the high energy image due to saturation, for example. Thus, to improve the accuracy of grid detection in embodiments of the present invention, the contrast from the low-energy image can be obtained first and then used to identify edges of the grid pattern. As is shown in the logic flow of FIG. 2, the results of low-energy grid detection in grid detection and suppression step S114, including this contrast information, are part of the input to grid detection and suppression step S112 for the high-energy image data.

Grid Detection

Grid detection in steps S114 and S112 determines whether or not an antiscatter grid has been used to acquire the image and helps to determine the orientation of the grid and other variables. Preferably, any grid detection should be fast and robust. This helps to speed processing and to prevent incorrect application of suppression filters. For successful grid suppression processing in general, a number of parameters associated with the type of grid that is used need to be identified, such as grid orientation, frequency, total energy, and energy coherence, for example. For dual energy grid detection, initial grid detection processing is first performed on the low-energy image, due to its significantly improved contrast over the high-energy image.

Grid lines within the image are usually approximately parallel to either the x axis (vertical direction) or the y axis (horizontal direction, orthogonal to the x axis). For this reason, it is sufficient to apply only one-dimensional (1-D) grid detection and suppression in the corresponding orientation. Even where grid lines are not parallel to either the x axis or the y axis, there is at least one dominant orientation between the x and y directions, in which the grid frequency is measured at a higher accuracy; 1-D grid suppression in this dominant orientation can substantially reduce the magnitude of the grid lines. Therefore, 1-D grid detection routines are conducted along both the x and y axes of the image. Then, only the dominant grid orientation is chosen for the suppression process.

Figure 3:
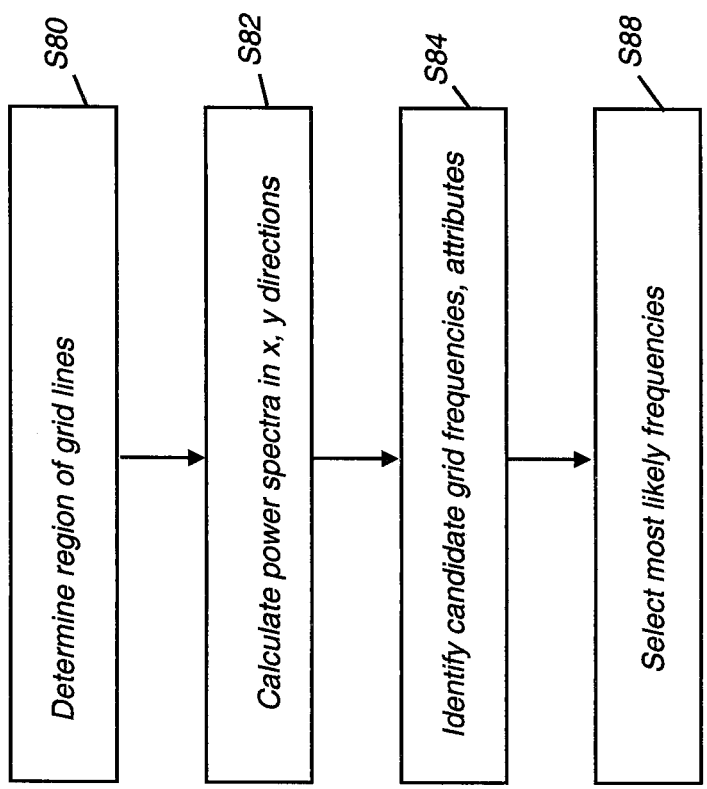
FIG. 3 shows steps for grid detection in one embodiment.

As seen in FIG. 3, grid detection processing has four steps:
(1) a determination step S80 that defines the image region for analysis, also referred to as the region of grid lines (ROG);
(2) a power spectra step S82 that obtains two 1-D power (energy) spectra, one in the x direction and the other in the orthogonal y direction across the image region;
(3) a candidate identification step S84 that identifies the candidate grid frequencies and their associated parameters; and
(4) a selection step S88 that provides recognition of the most likely grid frequencies.

In determination step S80, a region of the image is selected for grid detection. This selection process depends on a number of factors, such as image size, detection threshold, accuracy, speed and image representation, for example. Because the detection method is based upon the frequency spectra in the image, the well known fast Fourier transform (FFT) technique is utilized. The region can be the whole image. If the image size is not a number of an exact integer power of 2, zero-padding should be used in order to take advantage of the FFT method for spectral analysis. For example, an image of 2,048×2,500 pixels should be padded with 2,048×1,596 zeros to create an image of 2,048×4,096 pixels.

Taking the whole image for analysis can be computationally expensive, however, and may be unnecessary. When the grid lines are so prominent in an image that their presence becomes quite objectionable, the spectrum of a small image region can be sufficient for reliably identifying the grid frequency. For this reason, a small and very active region of grid lines (ROG) is extracted from the image for spectral analysis. The size of the ROG is determined empirically, as a trade-off between computation efficiency and frequency resolution; a smaller ROG size yields improved efficiency, but detection accuracy suffers. On the other hand, a larger ROG reduces computation efficiency but improves frequency resolution. In practice, a square ROG of an integer number of $2^n$ pixels, such as 1,024×1,024 is usually chosen.

Still referring to the process shown in FIG. 3, one way to determine the most active ROG is to use the regional average of pixel intensities. Since the more direct exposure regions are composed of pixels of either higher or lower intensities depending on the image polarity, a survey of the averaged intensity of all the pixels inside each ROG within the image indicates the most active ROG. The original image can be used for this survey process. However, to improve the computation efficiency, both the image and the ROG are subsampled to a smaller size and calculation is conducted using the sub-sampled image. After the intensity average of the pixels within each ROG is obtained, the ROG having the minimum average is selected for white-bone images (that is, where denser materials are indicated by higher pixel intensities), or, conversely, the ROG with the maximum average is selected for black-bone images. The selected ROG is passed to the next step of the detection stage for FFT spectral analysis. Since there are often some pixels in the close proximity of the image boundaries which are not directly related to x-ray image formation, such as the serial number of the phosphor screen for CR images or the information texts, these pixels are excluded from the search process.

Following ROG identification in step S80, FFT processing is conducted in step S82 and two 1-D power spectra are obtained for the selected most active ROG or, optionally, for the zero-padded whole image. The two 1-D power spectra correspond to the energy of the grid lines in the x direction and the y direction, respectively. There are a number of preferred approaches for obtaining the power spectrum. One approach takes two-dimensional (2-D) FFT followed by calculation of the magnitude square of the transform for energy spectra. Since the grid lines in the image are parallel to each other, a relatively high coherent grid energy in terms of line(s) can be observed in the 2-D power spectrum. Two profiles are readily available by averaging the 2-D spectrum along pixel rows and the columns, respectively. This averaging process is essentially an evidence accumulation process. It also reduces noise and therefore provides a more robust measure of the grid frequency(s).

In most cases, grid lines in the image are parallel to either the x axis or the y axis. Therefore, any line corresponding to the grid frequency in the power spectrum is also parallel to one of these orthogonal axes. In this case, one of the two averaged 1-D profiles can provide sufficient information regarding the grid characteristics. However, if the grid lines are not parallel to either the x axis or the y axis, the line(s) in the power spectrum are not parallel to either axis. In this case, the grid characteristics can be obtained using a second approach that calculates power spectra utilizing only a 1-D FFT. To reliably identify the peak locations in the power spectra, the size of the input image (most active ROG) should be reasonably large, however, a large image size needs more expensive 2-D FFT calculation. Based on the actual situation, the second approach only takes the 1-D FFT of a number of line samples in both the x direction and the y direction. Then, all the 1-D power spectra of each sampled line are averaged in either direction separately. This process of evidence accumulation can improve the detection robustness. The sampling can be taken at intervals, such as at every 1, 2, 3, . . . n rows (columns) of the image (wherein n is an integer).

Still referring to FIG. 3, candidate identification step S84 uses a search method to find all the candidate peaks and their associated parameters from the two averaged 1-D power spectra. For this purpose, some pre-processing is necessary. Since the pixel intensities of the input image are real numbers, the negative half of the FFT is simply the complex conjugate of the positive half, therefore the power spectra are symmetric about its center. This allows only the positive half to be used for the subsequent steps without losing any information. To reduce noise, a one dimensional Gaussian convolution kernel is applied for spectrum smoothing. For robust peak detection and peak energy calculation, the low-frequency background needs to be identified and subtracted from the smoothed spectra. One advantageous way of doing this is to use a morphological opening filter with a circular kernel. The size of the circular kernel should be several times larger than the widest peak width in order to minimize the error of energy calculation. For both Gaussian smoothing and morphological operations, mirroring of the data points at the two ends of the 1-D spectra is used, since the spectra themselves are periodic.

After all the pre-processing is completed, a search for all the local peaks greater than a predetermined magnitude in the spectra is conducted for the purpose of skipping peaks at very low frequency. A number of parameters related to the characteristics of the peaks are therefore calculated. These characteristics can include peak location (frequency), peak magnitude, half width of full maximum, total energy, grid orientation, and so on. These candidate peaks are sorted based on their energy, and only a predetermined number of peaks with higher energies in each power spectra are passed to the next step for analysis.

Step S88 of the grid detection process in FIG. 3 involves the calculation of figures-of-merit (FOMs) for each peak, wherein the most likely grid frequencies are recognized. In one embodiment, calculation and use of FOM values is similar to that described in commonly assigned U.S. Pat. No. 6,269,176 entitled "Method for X-ray Antiscatter Grid Detection and Suppression in Digital Radiography" to Barski et al.

It is mentioned that peak search can also be conducted directly in the 2-D FFT space, in which case a 2-D morphological filter can be used. Since the grid detection process is essentially finding the peaks in either the 1-D or 2-D power spectra, or equivalently, function optimization, one can use many other methods for peak identification instead of using the morphology filter. For example, golden section search, parabolic interpolation based Brent's search, first derivative-based search, downhill simplex method, Powell's method, and conjugate gradient method could optionally be used. These methods are familiar to those skilled in the image analysis arts.

Once the grid frequency for the low-energy image is identified, this same information can be used with the high-energy image data. Optionally, separate processing of the high-energy image data can be performed and checked against processing results from the low-energy image to validate grid detection results.

Grid Suppression

Suppression of the grid lines requires balancing tradeoffs between lowering the perception of aliasing (a direct effect of the grid lines), and removing relevant image information due to the suppression process. One effective method uses an adaptive blurring process to suppress the grid lines via spatial convolution. Empirical observation from viewing numerous images containing stationary grids indicates that the perception of aliasing is lowest in regions of low signal (that is, where relatively fewer x-rays have penetrated through the patient and exposed the acquisition receptor). Aliasing is highest in regions of medium to higher signal, corresponding to higher image contrast. Often, it is desirable to see as much detail as possible in the low signal regions of the image. Therefore, the suppression algorithm preferably performs minimal alteration to the original image in low signal regions. This requirement correlates well with the fact that the grid line shadows are minimally visible in these regions.

Another factor in determining the degree of suppression required is the relative energy of the grid. As grid energy increases, a greater degree of suppression is required.

A third factor for the suppression algorithm is the design of the blurring kernels. The kernel needs to be small enough to facilitate fast processing and minimize the blurring of important structures in the image, and large enough to cover the grid line shadow. Therefore, in the preferred embodiment, the strategy for processing is to design appropriate blur kernels (such as a bank of kernels to be applied adaptively) as a function of pixel size, grid energy, grid frequency and the related span of grid frequencies (the half-width of the full maximum peak).

Using the method of the present invention, grid suppression can be executed differently for the low- and high-energy images in a dual energy imaging application. As noted earlier, the grid may be less visible in the high-energy image content, due to its poorer relative contrast.

Figure 4:
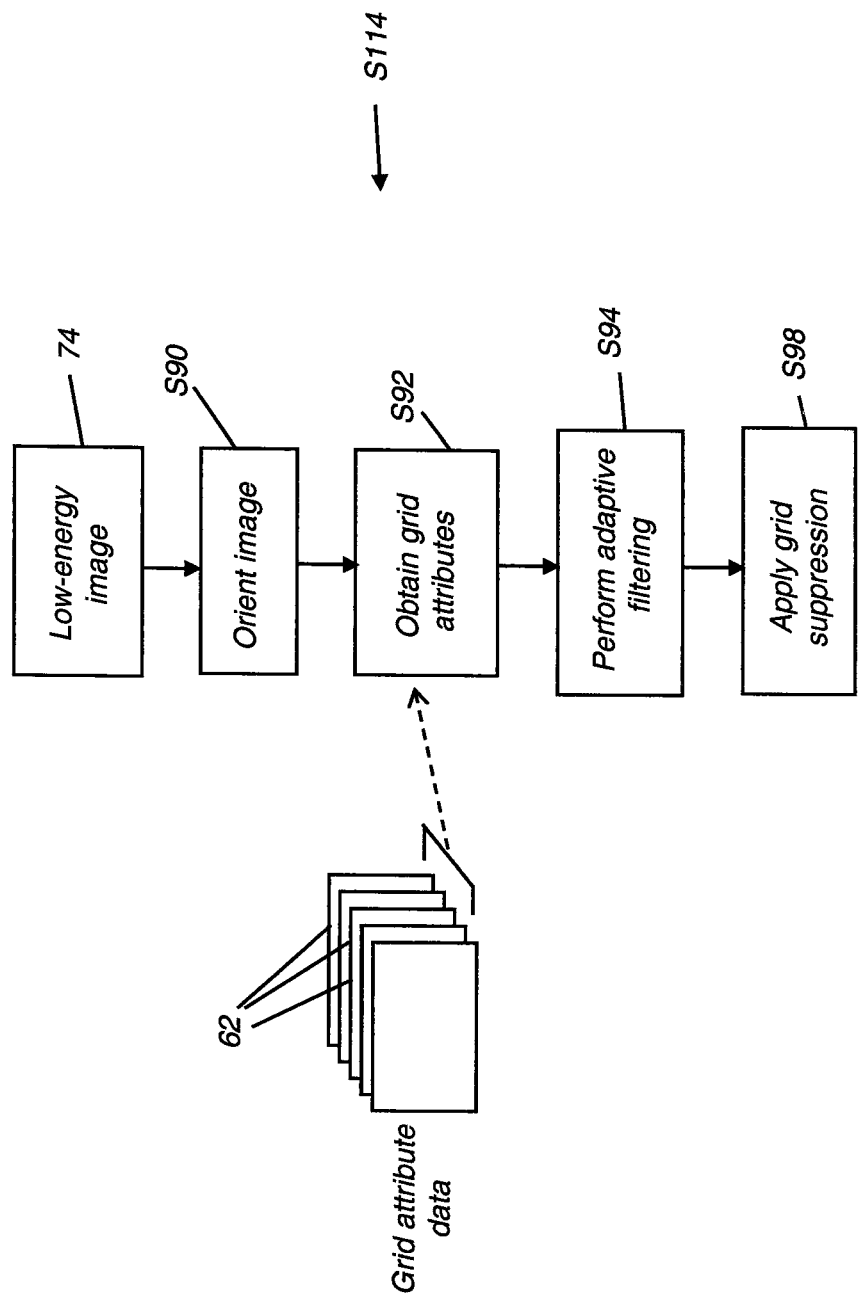
FIG. 4 shows steps used for grid detection and suppression for the low-energy image in a dual energy application.

Turning to FIG. 4, there is shown a sequence of steps for obtaining information on grid artifacts for a dual energy application. A low-energy image 74 is obtained from the DR detector as raw image data. An orientation step S90 orients the digital image data for grid detection and suppression. An obtain grid attributes step S92 then obtains information on the grid that is used. This step may refer to a standard library of grid attribute data 62 known for a specific manufacturer or site. Grid attribute data 62 can include values of grid frequency and height ratio information, for example. An adaptive filtering step S94 then processes the image data as described earlier. A grid suppression step S98 then performs the suppression of grid artifacts using adaptive suppression or other method.

Grid suppression in step S98 generally uses a notch filter, appropriately selected for the grid spacing and height ratio calculated for the grid. Adaptive grid suppression uses information from both the low-energy and high-energy image data, as obtained from the DR detector, so that information obtained from each of the images can be applied uniformly to both LE and HE images.

Figure 5:
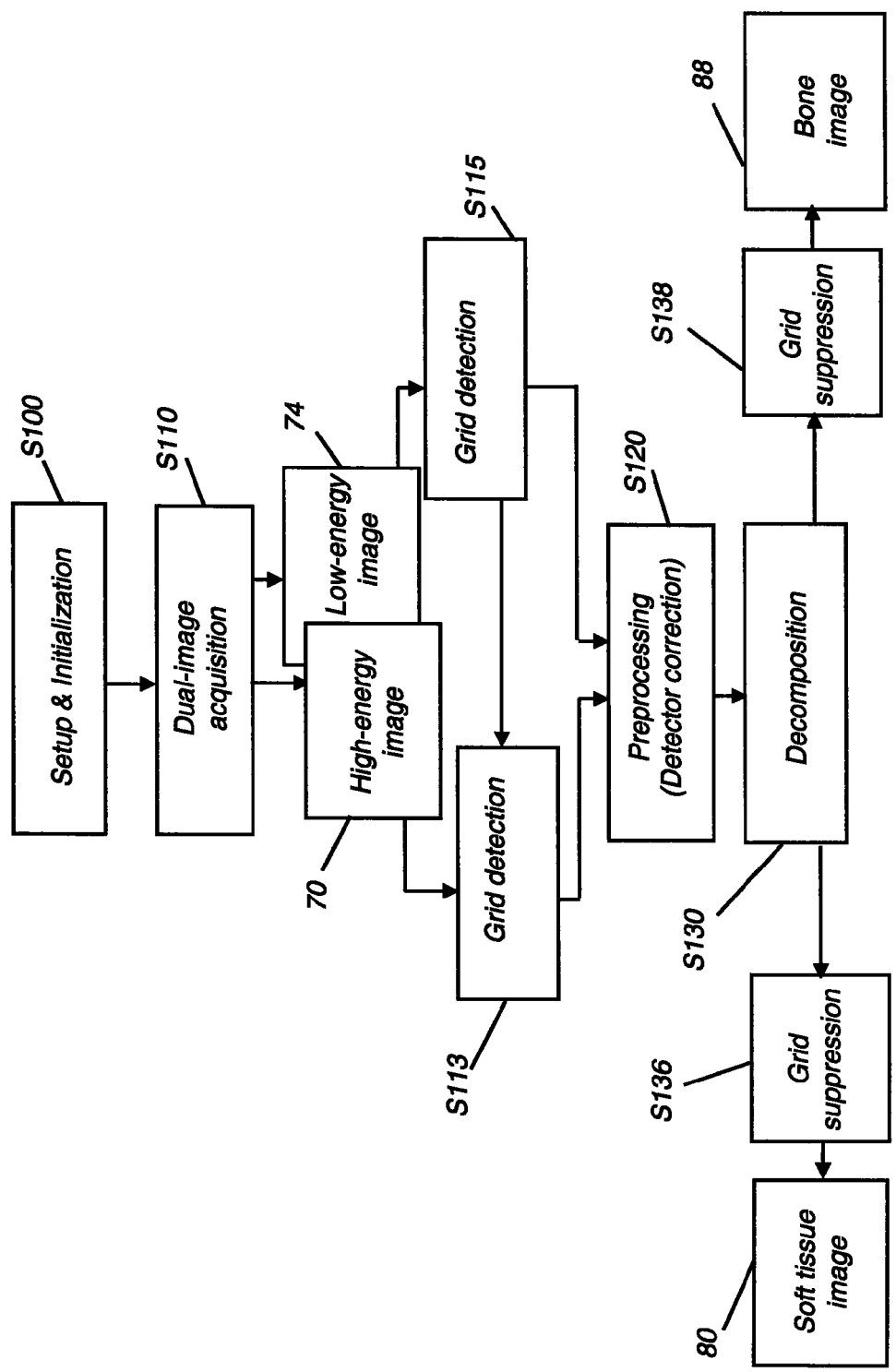
FIG. 5 shows steps for grid detection and suppression in an alternate embodiment in which suppression is applied following image decomposition, using grid detection performed prior to image pre-processing.

In an alternate embodiment, as shown in FIG. 5, a grid detection step S113 is applied to the high-energy image following image acquisition. Similarly, a grid detection step S115 is applied to the low-energy image data, prior to pre-processing. Grid detection steps S113 and S115 obtain the needed data for identifying grid artifacts in the raw data from both HE and LE images. However, grid suppression itself is not applied until after decomposition step S130. Grid suppression steps S136 and S138 apply, to the decomposed soft tissue and bone images, the information obtained earlier in grid detection steps S113 and S115. Again, this method allows grid detection information from both LE and HE images to be combined, although the results of grid detection are applied by suppression in subsequent processing.

Figure 6:
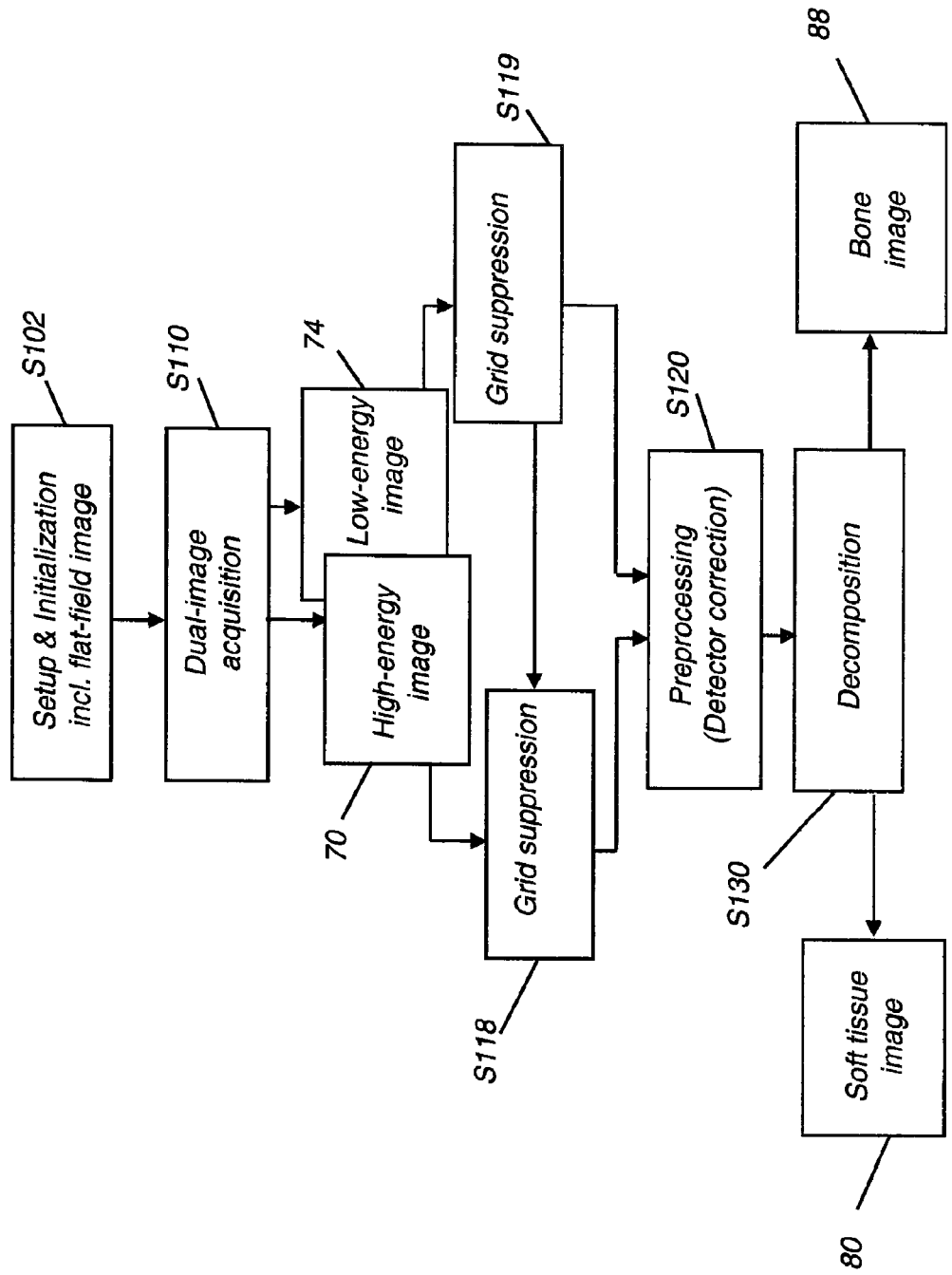
FIG. 6 is a logic flow diagram that shows an alternate embodiment in which setup and initialization includes obtaining one or more initial flat-field images, prior to positioning the detector behind the patient.

The logic flow diagram of FIG. 6 shows an alternate embodiment in which a setup and initialization step S102 includes one or more initial flat-field images, obtained prior to positioning the detector behind the patient. In this embodiment, the grid artifacts are identified as part of setup and initialization step S102, then applied to the raw image data for both HE and LE images as part of grid suppression steps S118 and S119, respectively.

As noted earlier, embodiments of the present invention can be applied to DE imaging as well as to other types of imaging that combine data from two or more exposures. This can include modalities that combine two or more images taken at different energy levels, at different angles, or with a change to some other variable between images, such as limited-angle digital tomosynthesis (DTS), in which, the relative positions of the x-ray source and detector are changed between each of two or more images, and the images are then combined to produce 3-D views of a subject. This can also be applied to cone beam computerized tomography (CBCT). With both DTS and CBCT methods, grid detection from the raw data has advantages, and it can be useful to provide grid suppression for the raw images (projection images), prior to their combination. For both DTS and CBCT modalities, grid artifacts may be more readily detected, since the grid direction is more likely to be in the direction of image rotation, or in the direction of relative detector movement between exposures.

While grid detection and suppression for multiple images can be used for stationary grids, the same techniques can be applied where reciprocating grids are used.

As described above, the embodiments of the invention may be executed in the form of computer-implemented processes and apparatus for practicing those processes. Embodiments of the invention may also be embodied in the form of computer program code containing instructions embodied in tangible media, such as portable memory devices, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits for carrying out the process of the present invention.

Referring to FIG. 7, there is shown a schematic diagram of an imaging apparatus 60 for providing dual energy (DE) imaging of a patient 12 or other subject according to an embodiment of the present invention. An x-ray tube 20 provides the needed exposure radiation for imaging, under the control of control circuitry 30 that has an operator console 32 for entry of setup and operation commands. X-ray tube 20 has a collimator 26 that controls the angular and spatial distribution of radiation that is provided. Imaging apparatus 60 uses a single DR detector 40 that has a grid 42 for scatter compensation. A DR imaging processor 48 obtains the digital data from DR detector 40 for each exposure and performs the image processing steps for DE imaging, as described earlier with reference to FIGS. 1-6. A display 46 in communication with DR imaging processor 48, or other output device, then displays each obtained image. A computer-accessible memory 50 enables processing and storage of the obtained and processed image data and can include magnetic, electronic, optical, or other storage media. The memory itself can be a random-access device, for short-term storage, or an optical or magnetic storage unit that is suitable for longer-term storage.

While the invention has been described with reference to exemplary embodiments in use with DE imaging, it will be understood by those skilled in the art that various changes may be made and equivalents may be substituted for elements thereof without departing from the scope of the invention. In particular, a number of changes would be needed to adapt embodiments of the present invention to the task of DTS or CBCT imaging, as described earlier in the background section. In addition, many modifications may be made to adapt a particular situation or material to the teachings of the invention without departing from the essential scope thereof Therefore, it is intended that the invention not be limited to the particular embodiment disclosed as the best mode contemplated for carrying out this invention, but that the invention will include other embodiments. Moreover, where used, the use of the terms first, second, etc. do not denote any order or importance, but rather the terms first, second, etc. are used to distinguish one element from another.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive.

PARTS LIST

12. Patient
20. X-ray tube
26. Collimator
30. Control circuitry
32. Operator console
40. DR detector
42. Grid
46. Display
48. DR imaging processor
50. Memory
60. Imaging apparatus
62. Grid attribute data
70. High-energy image
74. Low-energy image
80. Soft-tissue image
88. Bone tissue image
S80. Determination step
S82. Power spectra step
S84. Candidate identification step
S88. Selection step
S90. Orientation step
S92. Obtain grid attributes step
S94. Adaptive filtering step
S98. Grid suppression step
S100, S102. Setup and initialization step
S110. Image acquisition step
S112, S114. Grid detection and suppression step
S113, S115. Grid detection step
S118, S119. Grid suppression step
S120. Preprocessing step
S130 Decomposition step
S132, S134. Post-processing step
S136, S138. Grid suppression step

What is claimed is:

1. A processor-implemented method for providing a diagnostic image as a combination of two or more images, executed at least in part using a processor, comprising:
   obtaining at least first and second image data of a subject;
   analyzing, using the processor, both the first and second image data to identify at least grid orientation and spacing;
   applying grid suppression to the first and second image data;
   preprocessing the grid suppressed first and second image data;
   combining the grid suppressed first and second image data and decomposing the combined data to obtain one or more diagnostic images for display; and
   displaying, storing or transmitting the one or more diagnostic images.

2. The method of claim 1 wherein obtaining the at least first and second image data comprises obtaining the first image data at a first exposure and obtaining the second image data at a second exposure, wherein the second exposure is higher than the first exposure and of shorter duration.

3. The method of claim 2 wherein the contrast from the first image data is used for analyzing the second image data to identify at least the grid orientation and spacing.

4. The method of claim 1 wherein obtaining the at least first and second image data comprises obtaining the first image data at a first angle between a detector and a radiation source and obtaining the second image data at a second angle, different from the first angle.

5. The method of claim 1 wherein decomposing the combined image data provides soft tissue and bone images.

6. The method of claim 1 wherein applying grid suppression further comprises obtaining stored grid attribute data.

7. The method of claim 1 wherein the image detector is a digital radiography detector.

8. The method of claim 1 wherein analyzing both the first and second image data to identify at least grid orientation and spacing comprises:
   defining a region of the image for analysis;
   obtaining power spectra in at least two directions across the defined region;
   identifying candidate grid frequencies according to the obtained power spectra; and
   selecting the most likely frequencies from the candidate grid frequencies.

9. The method of claim 8 wherein obtaining power spectra comprises applying a fast Fourier Transform.

10. The method of claim 8 wherein selecting the most likely grid frequencies comprises calculating figures of merit for peak values in the power spectra.

11. The method of claim 1, wherein applying grid suppression to the first and second image data includes performing an adaptive blurring process to suppress the grid via spatial convolution.

12. A processor-implemented method for providing a diagnostic image as a combination of two or more images, comprising:
   obtaining at least first and second image data of a subject;
   analyzing, via a processor, both the first and second image data to identify at least grid orientation and spacing;
   preprocessing the first and second image data; and
   combining the first and second image data, applying grid suppression according to the analyzed grid orientation and spacing, and decomposing the combined data to obtain one or more diagnostic images; and
   displaying, storing, or transmitting the one or more diagnostic images that are obtained.

13. The method of claim 12 wherein analyzing both the first and second image data to identify at least grid orientation and spacing comprises comparing grid information obtained from images obtained at different energy levels.

14. A processor-implemented method for providing a diagnostic image as a combination of two or more images, executed at least in part on a computer, comprising:
   obtaining at least first and second image data of a subject;
   analyzing, via a processor, both the first and second image data to identify at least grid orientation and spacing;
   preprocessing the first and second image data; and
   combining the first and second image data and decomposing the combined data;
   applying grid suppression to the decomposed image results to provide separate images of soft tissue and of bone; and
   displaying the soft tissue and bone images on a display that is associated with the computer.

15. The method of claim 14 wherein the image data is obtained by means of a digital radiography detector.

* * * * *

UNITED STATES PATENT AND TRADEMARK OFFICE
CERTIFICATE OF CORRECTION

| | | |
|---|---|---|
| PATENT NO. | : 8,718,348 B2 | Page 1 of 1 |
| APPLICATION NO. | : 12/840351 | |
| DATED | : May 6, 2014 | |
| INVENTOR(S) | : David H. Foos et al. | |

It is certified that error appears in the above-identified patent and that said Letters Patent is hereby corrected as shown below:

On the Title Page, Item (75) Inventors:  Inventors should read -- David H. Foos, Webster, NY (US); John Yorkston, Penfield, NY (US); Xiaohui Wang, Pittsford, NY (US) --

Signed and Sealed this
Fourteenth Day of April, 2015

Michelle K. Lee
*Director of the United States Patent and Trademark Office*